United States Patent [19]

Kaplan et al.

[11] Patent Number: 4,792,566

[45] Date of Patent: Dec. 20, 1988

[54] IN-VIAL DEPOSITION OF 7-(DIMETHYLAMINOMETHYLENE)AMINO-9α-METHOXYMITOSANE

[75] Inventors: Murray A. Kaplan, Syracuse, N.Y.; Dolatrai M. Vyas, Madison, Conn.; Nagaswara R. Palepu, Liverpool, N.Y.; Chih-Ming J. Chen, Stanhope, N.J.

[73] Assignee: Bristol-Myers Company, New York, N.Y.

[21] Appl. No.: 863,202

[22] Filed: May 14, 1986

Related U.S. Application Data

[63] Continuation-in-part of Ser. No. 705,243, Feb. 25, 1985, abandoned.

[51] Int. Cl.$^4$ ............................................. A61K 31/40
[52] U.S. Cl. ..................................................... 514/410
[58] Field of Search ........................................ 514/410

[56] References Cited

U.S. PATENT DOCUMENTS

4,487,769  12/1984  Vyas et al. ........................ 514/410

FOREIGN PATENT DOCUMENTS

896963  6/1982  Belgium ............................ 514/410

Primary Examiner—James H. Reamer
Attorney, Agent, or Firm—David M. Morse

[57] ABSTRACT

There is disclosed a process for the in-vial deposition of 7-(dimethylaminomethylene)amino-9a-methoxymitosane in sterile unit dosage form. A solution of this compound is introduced into a sterile vial in a solution of tertiary-butanol. The tertiary-butanol is then removed, e.g., by evaporation or lyophilization, and the vial is closed by appropriate means. The thus deposited material can contain up to 0.5 mole equivalent of tertiary-butanol as a hemi-solvate and is very stable to heat.

18 Claims, No Drawings

IN-VIAL DEPOSITION OF 7-(DIMETHYLAMINOMETHYLENE)AMINO-9α-METHOXYMITOSANE

CROSS-REFERENCE TO RELATED APPLICATION

This application is a continuation-in-part of application Ser. No. 705,243, filed Feb. 25, 1985 now abandoned.

FIELD OF THE INVENTION

The present invention relates to a novel process for the in-vial deposition of 7-(dimethylaminomethylene)amino-9a-methoxymitosane.

DESCRIPTION OF THE PRIOR ART

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin®Bristol Laboratories, Syracuse, N.Y. 13201, Physicians' Desk Reference 38th Edition, 1984, p. 750). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7,9a-dimethoxymitosane, by reaction with ammonia to the latter, 7-amino-9a-methoxymitosane. Displacement of the 7-methoxy group of mitomycin A has proven to be a reaction of considerable interest in the preparation of antitumor active derivatives of mitomycin C. The following articles and patents each deals with the conversion of mitomycin A to a 7-substituted amino mitomycin C derivative having antitumor activity.

Matsui et al "The Journal of Antibiotics", XXI, 189–198 (1968)

Kinoshita et al "J. Med. Chem." 14, 103–109 (1971)

Iyengar et al "J. Med. Chem." 24, 975–981 (1981)

Iyengar, Sami, Remers, and Bradner, Abstracts of Papers—Annual Meeting of the American Chemical Society, Las Vegas, Nev., March 1982, Abstract No. MEDI 72.

Sasaki, et al Internat. J. Pharm., 1983, 15, 49.

The following patents deal with the preparation of 7-substituted aminomitosane derivatives by the reaction of mitomycin A, mitomycin B, or an $N^{1a}$-substituted derivative thereof with a primary or secondary amine:

Cosulich et al, U.S. Pat. No. 3,332,944, patented July 25, 1967.

Matsui et al, U.S. Pat. No. 3,420,846, patented Jan. 7, 1969.

Matsui et al, U.S. Pat. No. 3,450,705, patented June 17, 1969.

Matsui et al. U.S. Pat. No. 3,514,452, patented May 26, 1970.

Nakano et al, U.S. Pat. No. 4,231,936, patented Nov. 4, 1980

Remers, U.S. Pat. No. 4,268,676, patented May 19, 1981.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al Abst. of the Annual Meeting of Amer. Soc. for Microbiology 1982. Abs. 028).

Belgian Pat. No. 896,963, the disclosure of which is incorporated herein by reference, discloses a novel group of monoguanidino, or mono- and bis-amidino analogs of mitomycin C in which either or both the 7-amino nitrogen atom and the $N^{10}$carbamoyl nitrogen atom of mitomycin C are part of an amidino substituent or the 7-amino nitrogen is part of a guanidino group. One such compound, prepared as described in Examples 8 and 15 of that patent, is the compound 7-(dimethylaminomethylene)amino-9a-methoxymitosane which has the following structure:

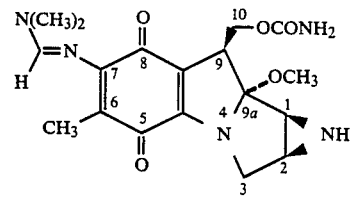

This compound, obtained as an amorphous solid, has a high activity against P-388 murine leukemia, exceeding that of mitomycin C both in terms of maximum effect and milligram potency (comparative dosage sizes for equivalent effects). However, it is generally unstable at 25°–56° C. A convenient means for providing this compound in a sterile vial in unit dosage form suitable for reconstitution with a parenteral vehicle has not hitherto been available. Since extremely small amounts of 7-(dimethylaminomethylene)amino-9a-methoxymitosane are utilized in unit dosage form and because of the extremely high toxicity of this compound, it is undesirable to manipulate the compound in bulk form, i.e., as a dry powder. Further, since the compound is unstable in water, aqueous solutions cannot be used to introduce the compound into a sterile vial in unit dosage form.

SUMMARY OF THE INVENTION

It has now been found that 7-(dimethylaminomethylene)amino-9a-methoxymitosane can be deposited in a vial in a sterile unit dosage form by introducing a solution of this compound in tertiary-butanol into a sterile vial. The tertiary-butanol is then removed, e.g., by evaporation or lyophilization, and the vial is closed by appropriate means such as by the use of a stopper. The thus deposited material can contain up to 0.5 mole equivalent of tertiary-butanol as a hemisolvate and is very stable to heat. It can be reconstituted when ready for use by admixing with a suitable parenteral vehicle.

Optionally, when lyophilization is to be used to remove the solvent, the solvent system may contain up to 10% by volume of ethanol. The ethanol lowers the freezing point of the lyophilization solvent system, thus increasing the efficiency of the process.

DETAILED DESCRIPTION OF THE INVENTION

The 7-(dimethylaminomethylene)amino-9a-methoxymitosane useful in the practice of this invention can be amorphous or crystalline.

Amorphous 7-(dimethylaminomethylene)amino-9a-methoxymitosane is prepared by the procedures of Examples 8 and 15 of Belgian Pat. No. 896,963. These procedures are described below.

PROCEDURE OF EXAMPLE 8 OF BELGIAN PAT. NO. 896,963

Compound I, 7-[(dimethylamino)methylene]amino-$N^{10}$-(dimethylamino)methylene-9a-methoxymitosane, was prepared as follows:

To a suspension of 500 mg (1.50 mM) of mitomycin C in 25 ml chloroform was added in total 9.6 ml (2.4 ml portions at 0, 18, 21 and 23 hours) of N,N-dimethylformamide dimethyl acetal and the suspension was stirred at about 50° C. for 41 hours. Upon evaporation of the solvent and excess reagent under reduced pressure, a dark green residue was obtained; tlc (methylene chloride/methanol 20:1) revealed the absence of mitomycin C and the presence of two new green components (Rf=0.16 and 0.22). The major component (Rf=0.16) was isolated by flash chromatography; using methylene chloride/methanol 20:1 as the eluant, as a green solid (340 mg 51.5%), which upon dissolution in diethyl ether followed by an addition of hexane afforded Compound I as a dark green amorphous powder.

NMR (pyridine $d_5$, $\delta$); 2.18 (s, 3H), 2.70 (bs, 1H), 2.76 (s, 3H), 2.82 (s, 3H), 2.86 (s, 6H), 3.22 (s, 3H), 3.30 (bs, 1H), 3.60 (d, J=12 Hz), 4.12 (dd, 1H, J=10, 4 Hz), 4.43 (d, 1H, J=12 Hz), 4.90 (bs, 1H), 5.10 (t, 1H, J=10 Hz), 5.52 (dd, 1H, J=10, 4 Hz), 7.85 (s, 1H), 8.64 (s, 1H).

IR(KBr) $v_{max}$, cm$^{-1}$: 3300, 2930, 1675, 1620, 1545, 1230, 1060.

UV($H_2O$) $\lambda_{max}$, nm: 390 and 244

Analysis: Calc'd for $C_{21}H_{28}N_6O_5$: C, 56.71; H, 6.08; N, 18.90. Found: C, 56.20; H, 6.28; N, 17.88.

7-(Dimethylaminomethylene)amino-9a-methoxymitosane (II) was prepared as follows:

To compound I (600 mg, 1.35 mM) dissolved in methanol (10 ml) was added aminodiphenylmethane (2.2 ml, 10.8 mM) and the resulting solution was stirred at 54° C. for 4 hours. The progress of the reaction was monitored by tlc (methylene chloride/methanol 90:10). At the end of 4 hours the starting material (RF=0.35) had disappeared and a major new green zone (Rf=0.29) appeared instead. The solution was concentrated at reduced pressure and the resulting syrup was flash chromatographed (25 g silica gel) using methylene chloride/methanol 20:1 as the eluant. Fractions containing the green component (Rf=0.29) were pooled, dried ($Na_2SO_4$) and concentrated. Compound II was obtained as an amorphous solid (215 mg, 41%).

NMR (pyridine $d_5$, $\delta$): 2.18 (s, 3H), 2.70 (bs, 1H), 2.80 (s, 3H), 2.88 (s, 3H), 3.08 (bs, 1H), 3.24 (s, 3H), 3.56 (bd, 1H, J=12 Hz), 4.00 (dd, 1H), 4.44 (d, 1H, J=12 Hz), 5.06 (t, 1H, J=10 Hz), 5.56 (dd, 1H, J=10, 4 Hz), 7.58 (bs, 2H), 7.88 (s, 1H).

IR (KBr) $v_{max}$, cm$^{-1}$: 3300–3450, 2960–2910, 1715, 1620, 1535, 1050.

UV ($H_2O$) $\lambda_{max}$, nm: 390 and 226

Anal. Calc'd for $C_{18}H_{23}N_5O_5$: C, 55.48; H, 5.91; N, 17.98 Found: C, 54.83; H, 5.67; N, 16.90.

PROCEDURE OF EXAMPLE 15 OF BELGIAN PAT. NO. 896,963

A 0.5M solution of N,N-dimethylchloromethyleniminium chloride was prepared by dropwise addition of oxalyl chloride (1.57 g, 12.5 mmol) at 0° C. to a solution of dimethylformamide (915 mg. 12.5 mmol) in 25 ml of $CHCl_3$ followed by stirring at room temperature for 30 minutes. Separately, a solution of mitomycin C (334 mg, 1 mmol) in 5 ml of dimethylformamide was added to a suspension of NaH (36 mg, 1.5 mmol) in 3 ml of dimethylformamide. The solution was stirred at room temperature for 20 minutes and cooled to $-40°\sim50°$ C. and the above solution of N,N-dimethylchloromethyleniminium chloride (3 ml, 1.5 mmol) was then added. Additional NaH (18 mg, 0.75 mmol) was added after 10 minutes of stirring at $-40°$ C. The solution was kept at $-40°$ C. for 1 hour and then diluted with $CH_2Cl_2$ and filtered. The residue obtained after evaporation of the filtrate was chromatographed by thin layer chromatography (TLC) on silic gel (10% $CH_3OH$—$CH_2Cl$ as elutant). Extraction of the major green band yielded 78 mg (43% based on the recovered mitomycin C) of an amorphous solid whose NMR spectrum and TLC behavior were identical to those of Compound II prepared as described above.

Amorphous 7-(dimethylaminomethylene)amino-9a-methoxymitosane can be converted to the crystalline form by dissolving it in acetone and/or ethanol and adding this solution to ether. It is preferred to add the solution over an extended period of time, e.g., 20 minutes. An alternative procedure for the preparation of crystalline 7-(dimethylaminomethylene)amino-9a-methoxymitosane is to slurry a quantity of amorphous 7-(dimethylaminomethylene)amino-9a-methoxymitosane in ethyl ether and then to add a small amount of crystalline 7-(dimethylaminomethylene)amino-9a-methoxymitosane. This results in transformation of the amorphous 7-(dimethylaminomethylene)amino-9a-methoxymitosane to the crystalline form.

Solutions of 7-(dimethylaminomethylene)amino-9a-methoxymitosane in tertiary-butanol or in tertiary-butanol containing up to 20% by weight of ethanol are readily prepared. The solutions are stable for at least 48 hours at 24° C. The solutions can be filtered sterilely and deposited in sterile vials. The solvent is removed via sublimation of yield a spongey, olive-green amorphous cake or, by controlled evaporation at a temperature of from 25°–30° C. to yield a dark-green mostly crystalline glass-like residue. Both solid forms are sufficiently stable for product dosage forms. There are several advantages associated with the use of tertiary-butanol in accordance with the practice of this invention. Tertiary-butanol provides a significantly stable solution that can be handled which is in contrast to an aqueous solution of 7-(dimethylaminomethylene)amino-9a-methoxymitosane, which is unstable. Further, tertiary-butanol is easily sublimable and can be readily removed. Still further, the tertiary-butanol deposits in the vial a much more stable form of 7-(dimethylaminomethylene)amino-9a-methoxymitosane than the amorphous form of 7-(dimethylaminomethylene)amino-9a-methoxymitosane previously described.

DESCRIPTION OF THE SPECIFIC EMBODIMENTS

The following examples constitute detailed procedures for the in-vial deposition of 7-(dimethylaminomethylene)amino-9a-methoxymitosane.

EXAMPLE 1

One g of 7-(dimethylaminomethylene)amino-9a-methoxymitosane as the free-base is slurried in tertiary-butanol, qs. to 200 ml for two hours in subdued, diffuse light at 26°-32° C. This provides a solution containing 5 mg/ml of 7-(dimethylaminomethylene)amino-9a-methoxymitosane. Under sterile conditions, this solution is passed under nitrogen pressure through a sterile, 0.22-micron Millipore filter designed for alcoholic solvents. The filtrate is collected in a sterile container. The solution temperature is not permitted to fall below 26° C. since tertiary-butanol can crystallize at below 25° C. Two ml of the solution are used to fill a number of sterile glass vials. The vials are partially stoppered with split, butyl rubber, lyophilization stoppers. The vials are placed in a sterile lyophilizer designed to condense tertiary-butanol and the contents are frozen at −40° C. The tertiary-butanol is then lyophilized or sublimed away under high vacuum at a shelf temperature of 24°-27° C. for 24 hours. The shelf temperature is then raised to 40°-50° C. and maintained for 3-5 hours. The shelf temperature is then lowered to 24°-27° C. and the vacuum is broken with sterile nitrogen. The vials are sealed with sterile aluminum seals. In each vial, there is obtained a fluffy, sponge-like, dark-green, mainly amorphous but partially crystalline, vial-cake, containing up to 0.5 mole equivalent of tertiary-butanol. The vials should be stored in the dark at 20°-26° C.

EXAMPLE 2

One g of 7-(dimethylaminomethylene)amino-9a-methoxymitosane as the free-base is slurried in tertiary-butanol, qs. to 100 ml, in subdued, diffuse light at 26°-32° C. for four hours to effect a solution. This provides a solution containing 10 mg of 7-(dimethylaminomethylene)amino-9a-methoxymitosane per ml of tertiary-butanol. Under sterile conditions, the solution is passed under nitrogen pressure through a sterile, 0.22-micron Millipore filter designed for use with alcoholic solvents. The filtrate is collected in a sterile container. One ml of the filtrate is placed in each of a number of sterile glass vials. The vials are partially stoppered with lyophilization stoppers and the vials are then placed in a sterile, vacuum oven designed to remove or condense tertiary-butanol. The shelf temperature is set at from 26°-30° C. and the vial contents are allowed to warm to this temperature. Using a source of variable vacuum, a vacuum over the vials is gradually increased over a 2-3 hour interval to approximately 24-27 inches of mercury. The tertiary-butanol evaporates at a rate of approximately 1 ml per five hours. 7-(dimethylaminomethylene)amino-9a-methoxymitosane crystallizes out of solution as its concentration in solution increases due to the slow evaporation of the tertiary butanol. The application of the vacuum at 25-27 inches of mercury is continued at a temperature of from 26°-30° C. shelf temperature for an additional 16-24 hours. A higher vacuum, i.e. 10-60 millitorr is then applied and the shelf temperature is raised to 40°-45° C. and maintained at this temperature for 4-6 hours. The shelf temperature is then lowered to 24° C. and the contents of the vials are allowed to cool to 24°-27° C. The vacuum is then broken with sterile nitrogen and the vials are sealed with sterile aluminum seals. A dense, dark-green and mostly crystalline vial-cake is obtained, containing up to about 0.5 mole equivalent of tertiary-butanol.

The stability of the thus deposited 7-(dimethylaminomethylene)amino-9a-methoxymitosane was determined by the following procedure: the required amounts of vials containing the deposited 7-(dimethylaminomethylene)amino-9a-methoxymitosane are placed at varied temperature stations. At each time-temperature interval, a vial containing the deposited 7-(dimethylaminomethylene)amino-9a-methoxymitosane is submitted for HPLC assay. The assay is reported as mcg/mg of 7-(dimethylaminomethylene)amino-9a-methoxymitosane activity. The results are set forth in Table 1. In this table, the material designated as "amorphous" is 7-(dimethylaminomethylene)amino-9a-methoxymitosane obtained by the process described in Belgian Pat. No. 396,963. This material was merely measured into the vials rather than being deposited therein in accordance with the practice of this invention. The designations "Example 1" and "Example 2" refer to 7-(dimethylaminomethylene)amino-9a-methoxymitosane deposited as described in Examples 1 and 2 of this application. Where more than one value appears, these are results for more than one test of 7-(dimethylaminomethylene)amino-9a-methoxymitosane deposited in accordance with that example.

TABLE 1

| Description of Material Being Tested | % Loss of 7-(Dimethylaminomethylene)amino-9a-methoxymitosane | | | | 4 Months @ 37° C. | 24 Hrs. @ 100° C. |
| --- | --- | --- | --- | --- | --- | --- |
| | 56° → | | | | | |
| | 1 Week | 2 Weeks | 4 Weeks | 8 Weeks | | |
| Amorphous | 14 | 25 | 41 | — | — | 90 |
| Example 1 | — | — | 1.9; 1.2; 0; 1.5-7.0 | 0-4.6 | 0 | 74 |
| Example 2 | — | 0 | 1.8; 0; 1.2; 0 | +3.8 | +6 | 27; 7 |

To reconstitute the tertiary-butanol in-vial deposited 7-(dimethylaminomethylene)amino-9a-methoxymitosane free-base, it is preferred to use an aqueous parenteral vehicle having a pH of 6.6 containing 0.01 mole of citrate buffer with 1 mg/ml of Pluronic F 68 or one containing 0.01 mole of L-valine with the pH adjusted to 6.5. Such reconstitution vehicles have been found to give acceptable utility times, i.e., at least three hours with less than 10% loss. In another preferred embodiment which achieves acceptable reconstitution utility time, the aqueous vehicle contains up to 30%, and more preferably, from 10-30% by weight of nicotinamide. Table 2 shows the effect of the incorporation of nicotinamide into the aqueous reconstitution vehicle.

TABLE 2

| Time (hrs.) | % of 7-(Dimethylaminomethylene) amino-9a-methoxymitosane Remaining | | |
|---|---|---|---|
| | 0% Nicotinamide | 10% Nicotinamide | 30% Nicotinamide |
| 0 | 100.0 | 100.0 | 100.0 |
| 1 | 88.7 | 94.1 | 96.5 |
| 2 | 83.6 | 91.5 | 92.8 |
| 3 | 81.2 | 90.5 | 94.2 |
| 4 | 79.0 | 89.0 | 93.3 |
| 5 | 77.0 | 88.4 | 92.5 |
| 6 | 74.8 | 86.9 | 91.6 |

EXAMPLE 3

Into a clean, dry and precalibrated container equipped with a stirrer, are placed 190 ml of tertiary-butanol and 10 ml of ethanol. One gram of 7-(dimethylaminomethylene)amino-9a-methoxymitosane as the free base is slurried into the solvent system and the contents are stirred for approximately one to two hours until all the 7-(dimethylaminomethylene)amino-9a-methoxymitosane is dissolved. This provides a solution containing 5 mg/ml of 7-(dimethylaminomethylene)amino-9a-methoxymitosane. Under sterile conditions, this solution is aseptically filtered, using an appropriate sterilized 0.22 micrometer filter into a sterilized container. The solution was used to fill a number of sterile glass vials, 1 ml of solution per vial. The vials are then placed in a lyophilizer equipped with a liquid nitrogen trap to protect the vacuum pump. The vials are subjected to freezing temperatures in the lyophilizer at $-20\pm2°$ C. for 45 minutes and are then heated to $4\pm2°$ C. and held for one hour. The vials are cooled to $-20\pm2°$ C. and when the warmest thermocouple reaches $-20\pm3°$ C., timing is started and held for three to four hours. Sublimation is then conducted at $-20\pm5°$ C. under a pressure of 100-200 microns for 24-28 hours. The first drying phase is then conducted at $25\pm5°$ C. under a pressure of 100-200 microns for 36-40 hours; and the second drying phase is conducted at $45\pm5°$ C., again under a pressure of 100-200 microns, for 6-8 hours. The vacuum is then shut off and sterile nitrogen is slowly bled into it. The vials are then sealed with appropriate stoppers and seals.

What is claimed is:

1. A process for the in-vial deposition of 7-(dimethylaminomethylene)amino-9a-methoxymitosane in sterile unit dosage form which comprises introducing a solution of 7-(dimethylaminomethylene)amino-9a-methoxymitosane in tertiary-butanol into a sterile vial and thereafter removing the tertiary-butanol.

2. A process as defined in claim 1 wherein said tertiary-butanol is removed by lyophilization.

3. A process as defined in claim 2 wherein said tertiary-butanol solution is frozen to $-40°$ C. and the tertiary-butanol is sublimed at high vacuum.

4. A process as defined in claim 1 wherein said tertiary-butanol is removed by evaporation.

5. A process as defined in claim 4 wherein said tertiary-butanol is evaporated under vacuum at a temperature of from 25°-30° C.

6. A process as defined in claim 1 wherein from 5-10 mg of 7-(dimethylaminomethylene)amino-9a-methoxymitosane are deposited in said vial.

7. A process as defined in claim 2 wherein from 5-10 mg of 7-(dimethylaminomethylene)amino-9a-methoxymitosane are deposited in said vial.

8. A process as defined in claim 3 wherein from 5-10 mg of 7-(dimethylaminomethylene)amino-9a-methoxymitosane are deposited in said vial.

9. A process as defined in claim 4 wherein from 5-10 mg of 7-(dimethylaminomethylene)amino-9a-methoxymitosane are deposited in said vial.

10. A process as defined in claim 5 wherein from 5-10 mg of 7-(dimethylaminomethylene)amino-9a-methoxymitosane are deposited in said vial.

11. A process as defined in claim 1 wherein said deposited 7-(dimethylaminomethylene)amino-9a-methoxymitosane is subsequently reconstituted with an aqueous parenteral vehicle.

12. A process as defined in claim 11 wherein said aqueous parenteral vehicle has a pH of 6.6 and includes 0.1 mole of citrate buffer.

13. A process as defined in claim 1 wherein said aqueous parenteral vehicle includes 0.1 mole of L-valine and the pH of the vehicle is 6.5.

14. A process as defined in claim 11 wherein said aqueous parenteral vehicle contains up to 30% by weight of nicotinamide.

15. A process as defined in claim 11 wherein said aqueous parenteral vehicle contains from 10-30% by weight of nicotinamide.

16. A process as defined in claim 2 wherein the solvent system contains up to 10% by volume of ethanol.

17. A process as defined in claim 3 wherein the solvent system contains up to 10% by volume of ethanol.

18. 7-(Dimethylaminomethylene)amino-9a-methoxymitosane containing up to 0.5 mole equivalent of tertiary-butanol.

* * * * *